(12) United States Patent
Shio et al.

(10) Patent No.: US 6,726,933 B2
(45) Date of Patent: Apr. 27, 2004

(54) ROD-SHAPED MESOPOROUS POWDER, HUMECTANT ADSORBING POWDER, AND COSMETIC PREPARATION USING THE SAME

(75) Inventors: Shoichiro Shio, Yokohama (JP); Asa Kimura, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/964,878

(22) Filed: Sep. 28, 2001

(65) Prior Publication Data

US 2002/0051802 A1 May 2, 2002

Related U.S. Application Data

(63) Continuation-in-part of application No. 09/077,416, filed as application No. PCT/JP97/03487 on Sep. 30, 1997.

(30) Foreign Application Priority Data

Sep. 30, 1996 (JP) ............................................. 8-278870
Feb. 18, 1997 (JP) ............................................. 9-50965

(51) Int. Cl.$^7$ ........................... A61K 7/035; A61K 9/14
(52) U.S. Cl. ......................... 424/489; 424/69; 424/401
(58) Field of Search ......................... 424/401, 69, 489

(56) References Cited

U.S. PATENT DOCUMENTS 5,057,296 A * 10/1991 Beck ........................... 423/277

OTHER PUBLICATIONS

Japanese Patent Office, "Patent Abstracts of Japan," Publication No.: 08/067578, Date of Publication: Mar. 12, 1996, Application No.: 07–179566, Filing Date: Jun. 21, 1995.

Lin, Hong–Ping, et al., "'Tubules–Within–a–Tubule' Hierarchical Order of Mesoporous Molecular Sieves in MCM–41," Science, Aug. 9, 1996, pp. 765–767, Vol 273, American Association of the Advancement of Science.

* cited by examiner

Primary Examiner—Thurman K. Page
Assistant Examiner—S. Howard
(74) Attorney, Agent, or Firm—Snider & Associates; Ronald R. Snider

(57) ABSTRACT

A rod-shaped mesoporous powder which is mainly composed of silicon oxide and has homogenous pore, and obtained by a process comprises, a dissolution step wherein a concentration of 0.3–1.2M of a silicate which is in the range of $0<SiO_2/Y_2O<2$ (Y: alkali metal atom) is dissolved in the presence of a cationic surfactant and the pH is 11 or more, a condensation step wherein the pH is adjusted to 10.5 or less within 30 minutes, a rod micelle is formed with said cationic surfactant and a silicate is condensed on said rod micelle, and a removal step wherein said cationic surfactant is removed from a micelle state condensation which has an outer shell made of the silicate by said condensation.

11 Claims, 9 Drawing Sheets

F I G. 1
F I G. 2

F I G. 5
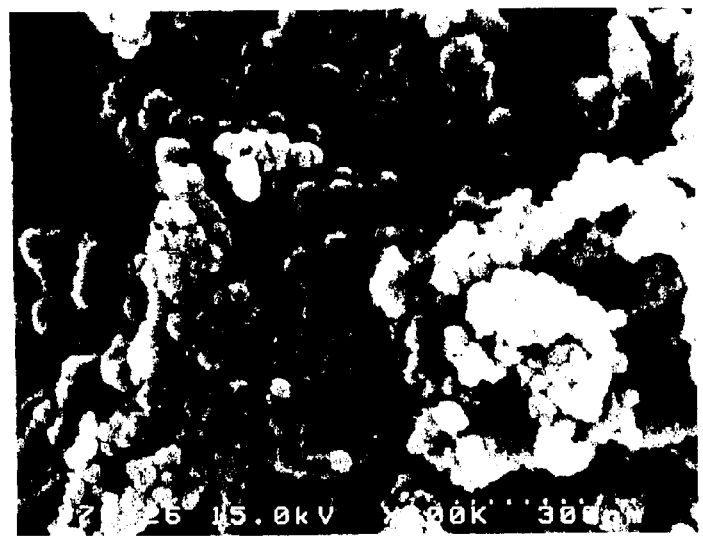
F I G. 6
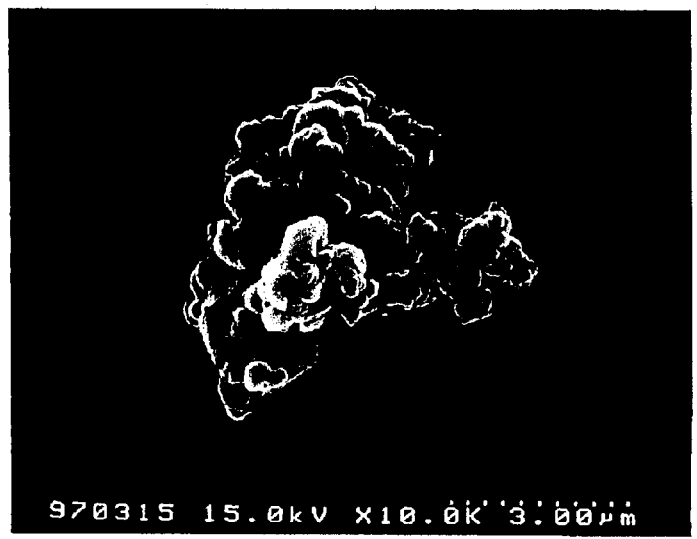

ROD-SHAPED MESOPOROUS POWDER, HUMECTANT ADSORBING POWDER, AND COSMETIC PREPARATION USING THE SAME

This application is Continuation-in-part Application of U.S. patent application Ser. No. 09/077,416 filed on Sep. 30, 1997, which is incorporated herein by reference.

TECHNICAL FIELD

The present invention relates to a rod-shaped mesoporous powder, a humectant adsorbing powder and a cosmetic preparation using the same, and in particular, relates to an improvement of a shape of the powder, and an improvement of shelf life of the cosmetic preparation using the same.

BACKGROUND ART

A so-called mesoporous powder which has a mesopore of 2 to 50 nm pore size attracts attention as an adsorbent of gas or liquid, or as a carrier of a catalyst.

For example, a mesoporous powder which is disclosed in Japanese Unexamined Patent Publication No. Hei 8-67578 is composed of a three-dimensional structure which is made of a silicate and has a relatively uniform pore of 1.5–10 nm.

As for a manufacturing process of the mesoporous powder, a process for forming a three-dimensional structure by introducing a surfactant to an interlayer of a layer silicate such as kanemite and removing the surfactant with calcination or by removing a surfactant after gathering a silicate around the surfactant which was gathered in liquid with micelle state and the like are developed.

However, a particle size of the mesoporous powder is prescribed to the particle size of the layer silicate in the former process which uses the layer silicate. Also, since the mesoporous powder is laminar, it is feared that fluid resistance per pore degree is increased in the case where the mesoporous powder is used as a column packing.

On the contrary, though examples of manufactured rod-shaped porous powders which are reported (Science Vol. 273 pp. 765–767), every rod porous powder has a considerably large size. In particular, the external diameter is approximately 3 μm and the pore size becomes big. This is far from mesoporous in size when the pure silicic porous powder does not contain aluminum. Therefore, a specific surface area becomes relatively small and there is a problem that the process is limited to use only for a molecular sieve. Also, a rod-shaped mesoporous powder of certain fine particle size can be manufactured in the case where aluminum is contained in the powder. However, it is feared that catalytic activity becomes high due to the presence of aluminum. This process is also unfavorable.

On the other hand, as a powder cosmetic preparation, there is a powder of a loose form such as a white powder, a baby powder, and a body powder, and solid form including an excipient for hardens.

These powder cosmetic preparations are widely used for makeup repair, and keeping the skin healthily due to the absorption of sweat and sebum by the powder.

In the prior art, the powdery cosmetic preparation included no water. Recently the importance of humectance has been recognized. As a result, it is desired to add humectant in a powdery cosmetic for good humectance.

However if a large mount of high water-absorbing material such as a humectant is compounded in a powder cosmetic preparation, the water-absorbing powder cosmetic preparation itself increases and the expansion and sweating may appear in the product.

Therefore, it was substantially impossible to blend a large amount of humectant to obtain the moisturing effect satisfactory, even if it is possible to blend small amount of humectant with a powder cosmetic preparation.

DISCLOSURE OF INVENTION

In view of the above-mentioned problems of the prior art, a first object of the present invention is to provide a rod-shaped mesoporous powder which is mainly comprised of silicon oxide and has homogenous pore.

Also, a second object of the present invention is to provide humectant adsorbed powder that can improve stabilization of a product and also has an excellent humectance, and a cosmetic preparation using the same.

As a result of diligent studies by the inventors for attaining the above-mentioned objects, it has been found that a fine diameter rod-shaped mesoporous powder can be obtained by reacting a silicate which has a specific ratio of silica/alkali metal under a specific concentration.

Namely, a rod-shaped mesoporous powder in accordance with the present invention is mainly composed of silicon oxide and has almost homogenous pore, and is obtained by a process which comprises the step of, a dissolution step wherein a concentration of 0.3–1.2M of a silicate which is in the range of $0<SiO_2/Y_2O<2$ (Y: alkali metal atom) is dissolved in the presence of a cationic surfactant and the pH is 11 or more, a condensation step wherein the pH is adjusted to 10.5 or less within 30 minutes, a rod micelle is formed with said cationic surfactant and a silicate is condensed on said rod micelle, and a removal step wherein said cationic surfactant is removed from a micelle state condensation which has an outer shell made of the silicate by said condensation.

Also, in said powder, it is preferable that whose outer diameter is 20–200 nm and a mesopore is elongated to its longer direction.

Also, in said powder, it is preferable that a primary particle is formed by aggregating two or more of rod substances in network state.

The humectant adsorbing powder in accordance with the present invention comprises the rod-shaped mesoporous powder and a humectant adsorbed in the powder.

Also, in said powder, it is preferable that the adsorption rate of said humectant is 1 to 90% by weight of the total of a humectant adsorbed powder.

When the adsorbing rate of the humectant falls below 1 wt %, the actual effect of the moisture disappears. When the adsorbing rate of the humectant exceeds 90 wt %, it exceeds the limit of the sweat and sebum absorption action of the powder.

Namely, a cosmetic preparation in accordance with the present invention comprises said humectant adsorbing powder.

Also, in said cosmetic preparation, it is preferable that the content of humectant adsorbing powder is 0.1 to 90% by weight of the total of a cosmetic preparation When the content of humectant absorbing powder falls below 0.1 wt %, the actual effect of said humectant absorbing powder is not sufficiently obtained. When the content of humectant absorbed powder exceeds 90 wt %, the product is hardly obtained.

BRIEF DESCRIPTION OF THE DRAWINGS

FIGS. 1–4 are explanatory views showing a relation between concentration of silicate and crystalline state.

FIG. 5 is an explanatory view showing a relation between addition rate of acid for pH control and crystalline state.

FIGS. 6 and 7 are explanatory views showing a relation between concentration of acid for pH control and crystalline state.

BEST MODE FOR CARRYING OUT THE INVENTION

Figure 3:

The present inventors studied about behavior of a water-soluble component in the case where silicate is dissolved with alkali.

In the case where the present inventors further studied, it was found that silicate can be dissolved even in the presence of the surfactant by prescribing the range of the silicate within $0<SiO_2/Na_2O<2$ and a non-laminar silicon oxide powder which has extremely high homogeneity can be obtained by separating silicate ion which is in the dissolution state on the micelle of the quaternary ammonium salt.

Solubility of the silicate is deteriorated and the solution is clouded by adding the cationic surfactant in the case where said $SiO_2/Y_2O$ is more than 2. Also, homogeneity of the powder which is finally obtained is influenced by accumulating the silicate particles which are in insoluble state on the micelle.

The solution is clouded due to the existence of the cationic surfactant and does not reach sufficiently dissolved state and a homogenous mesoporous powder can not be obtained in the case where water-glass and the like have more than 2 of $SiO_2/Y_2O$ are used as a raw material. As a technique for forming a mesoporous powder with the composition which has more than 2 of $SiO_2/Y_2$, the technique which is disclosed in Japanese Unexamined Patent Publication No. Hei 5-503499 is known. However, this existing the technique for preparing a mesoporous powder is together with an aluminum compound. There is no improvement of the catalytic activity with the aluminum compound.

Also, a rod-shaped mesoporous powder can be prepared by prescribing the concentration of the silicate within the specific range.

The preferable embodiments of the present invention will be explained in the following.

I. Rod-shaped Mesoporous Powder

The silicates used in the present invention are $0<SiO_2/Y_2O<2$ (Y: alkali metal atom). As examples of the alkali metal atom, in particular, Na or K is preferable because of availability.

The above-mentioned silicate can be formed by reacting the various "materials which contain silicon" with the alkali such as NaOH.

Examples of "materials which contain silicon", are silicon oxide, silicate, silicon alkoxide, water-glass and the like.

Examples of the silicate are $Na_2SiO_3$, $Na_4SiO_4$ and the like.

Examples of the silicon alkoxide are tetramethyl orthosilicate, tetraethyl orthosilicate, and the like. It is preferable to use these materials together with e.g., silicate, because these materials have low reactivity when used separately.

Also, as examples of the water-glass, JIS No.1, JIS No.2, JIS No.3 and the like are listed.

In this place, most of the "materials which contains silicon" have more than 2.0 of $SiO_2/Na_2O$ and it is difficult to manufacture a homogenous non-laminar silicon oxide powder. Accordingly, the silicate which can be displayed as $0<SiO_2/Na_2O<2$ can be obtained by adding and dissolving e.g., an alkali agent such as sodium hydroxide. The silicate used in the present invention has no difficulty in forming a mesoporous powder in the case where $SiO_2/Na_2O$ is less than 0.5. However, the silicate is wasted when there is an excess amount of the alkali agent in the compound. Also, the water solution is clouded and it is difficult completely dissolve and is difficult to form a homogeneous silicon oxide powder in the case where $SiO_2/Na_2O$ is more than 2. Therefore, the silicate used in the present invention is preferably $0<SiO_2/Y_2O<2$, and more preferably is $0.5 \leq SiO_2/Na_2O \leq 1.9$.

Cationic Surfactant

As an example of a cationic surfactant, a quaternary ammonium salt is preferable.

The quaternary ammonium salt is preferably an alkyl quaternary ammonium salt $[R_4N]X$ and a cyclic quaternary ammonium salt,

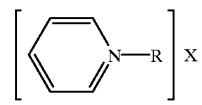

wherein in said quaternary ammonium salt, the quaternary ammonium salts which has a structure such as R: H, an alkyl group, an allyl group, a benzyl group, a phenyl group, a hydroxyl group and a hydroxyalkoxyl group, and X: $Cl^-$, $Br^-$, $I^-$ and $NO_3^-$.

These quaternary ammonium salts are required to form a rod micelle by adjusting the pH to 10.5 or less in the water solution.

In the case where R of the quaternary ammonium salt is the alkyl group having a carbon number more than 18, the rod-shaped powder is ready to be formed.

Also, in the case where R of the quaternary ammonium salt is the alkyl group having a carbon number of 18 or less, it is preferably used with 0.1–3 M of acid residue excluding silicon, e.g., salts of $Cl^-$, $Br^-$ and $I^-$ in order to form the rod-shaped powder.

Also, a process for manufacturing a mesoporous powder which is characterized in the present invention is constructed as follows.

Dissolution Step

The silicate and the cationic surfactant were mixed and the mixture was heated to room temperature or the temperature that both were dissolved. In the case where the pH in the time of the mixture was less than 11 or $SiO_2/Na_2O$ was equal to or more than 2, the pH was adjusted to 11 or more and $SiO_2/Na_2O$ was adjusted to less than 2 by adding the alkali agent.

A retention time required in this reaction may be relative short period which is required to increase to the temperature where both ingredients are dissolved.

A ratio of the cationic surfactant with respect to the silicate is preferably 0.02–1.0, and more preferably is 0.05–0.3 at molar ratio. An amount of a rod micelle of the cationic surfactant is small in the case where the ratio of the cationic surfactant to the silicate is less than 0.02 at molar ratio. Also, a large amount of the unreacted cationic surfactant remains when the ratio of the cationic surfactant to the silicate is more than 1.0 at molar ratio.

Condensation Step

An acid was added to the solution which was obtained in said dissolution step in order to adjust the pH to 10.5 or less.

As a result, a rod micelle was formed by gathering the cationic surfactant or its globular micelle. Also, silicate ion which was in dissolved state at a pH of 11 or more, was condensed at the pH of 10.5 or less, and the silicate was arranged around the outer periphery of the rod micelle of the cationic acid. The powder which has an arrangement of hexagonal structure can be formed by this manipulation. The above-mentioned effects are not displayed sufficiently in the case where the pH is more than 10.5.

Removal Step

The dispersing of said powder was separated and was filtrated. Then, the cationic surf actant was removed. Water-washing and calcination are listed as examples of this removal operation. The cationic surfactant was removed by this removal operation and thus a mesoporous powder was obtained.

Study of $SiO_2/Y_2O$

First, a study about $SiO_2/Y_2O$ which is characterized in the present invention was conducted.

Namely, a proper amount of sodium hydroxide (manufactured by Nacalai Tesque Co., Ltd.) of a guaranteed reagent was dissolved to 1 liter of ion-exchanged water. 300 g of silicon dioxide (#200, manufactured by Aerosil Co. Ltd) which is commercially available was added to the dissolution and was stirred. Sodium silicate was obtained by calcining the solution for 5 hours at 700° C.

Then, the present inventors prepared sodium silicate which has various types of $SiO_2/Na_2O$ which are shown in TABLE I and tried to manufacture a mesoporous powder using these sodium silicates as a raw material.

TABLE 1

| $SiO_2/Na_2O$ | 0.5 | 1.0 | 1.5 | 2.0 |
|---|---|---|---|---|
| pH | 12.05 | 11.95 | 11.65 | 11.35 |
| Dissolution state | Completely dissolved | Completely dissolved | Completely dissolved | Semi-transparent |
| Specific surface area ($m^2/g$) | 1066 | 1126 | 1142 | 1052 |

A measurement of X-ray diffraction was also conducted at the same time. This measurement was conducted by using JDX-350 manufactured by JEOL Ltd., at 2 degree (2 θ)/min. CuK α ray was used as an X-ray source. Slit breadth was 1 degree—0.2 mm—1 degree.

As a result of this experiment, it was confirmed from the result of X-ray diffraction that a hexagonal structure was formed in the case where sodium silicate was in dissolution state. However, a homogenous silicon oxide powder was sometimes not obtained in the case where sodium silicate was not completely dissolved.

As is clear from the TABLE shown above, $SiO_2/Na_2O$ is preferably less than 2.0. Accordingly, it is understood that an appropriate powder can not be manufactured in this way, when water-glass and the like which are more than 2.0 of $SiO_2/Na_2O$ are directly used.

Also, in the case where $SiO_2/Na_2O$ was 2, sodium silicate sometimes could not be dissolved and a hexagonal structure was not formed. And, about 1.9 of $SiO_2/Na_2O$ is preferable in particular to form the stable hexagonal structure.

Concentration of Silicate

It is preferable to adjust a concentration of silicate to form silicon oxide powder in the rod-shape in the present invention.

Namely, a prescribed mol of sodium metasilicate and behenyl trimethylammonium chloride (BTC) were dissolved to 1 liter of ion-exchanged water. The temperature at this time was maintained at 70° C. The pH value of the mixture was adjusted to 8–9 with 2N hydrochloric acid solution just after the dissolution. Then, the dissolution was filtrated and washed with water. A powder was obtained by calcining the solution for 3 hours at 700° C.

TABLE 2

Figure 4:
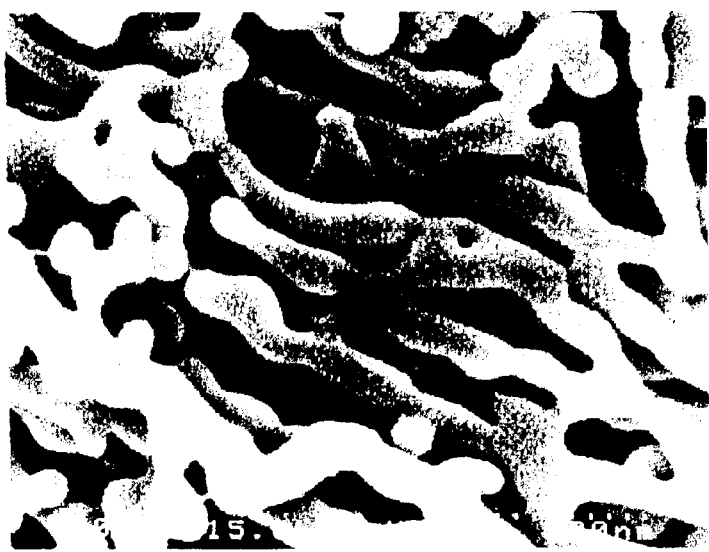

| Concentration of metasilicate (M) | 0.15 | 0.5 | 1.0 | 1.5 |
|---|---|---|---|---|
| BTC (M) | 0.03 | 0.1 | 0.2 | 0.3 |
| Property | Fine mesoporous FIG. 1 | Rod mesoporous FIG. 2 | Rod mesoporous FIG. 3 | Rod nonporous FIG. 4 |

As is clear from the result, the powder was mesoporous in the case where the concentration of the silicate was 0.15M, but the powder nevertheless became fine. Also, though the powder was rod-shaped in the case where the concentration of the silicate was 1.5M, there were almost no pores.

Then, it is possible to prepare a fine mesoporous powder in the case where the concentration of the silicate is 0.1M or more by the experiment of the inventors. Further, it was confirmed that a rod-shaped mesoporous powder was obtained with the concentration of 0.3 to 1.2M and a rod-shaped nonporous powder was obtained with the concentration of 1.2M or more, by adjusting the pH changing rate which will be described in the following.

Acid Addition Rate for pH Adjustment

It is preferable to adjust the addition rate of the acid for pH adjustment which was added at said condensation step in order that the powder can be formed with the rod-shape in the present invention.

Namely, 0.5 mol of sodium metasilicate and 0.1 mol of behenyl trimethylammonium chloride (BTC) were dissolved to 1 liter of ion-exchanged water as like the above. The temperature at this time was maintained at 70° C. The pH value of the mixture was adjusted to 8–9 with 2N hydrochloric acid solution just after the dissolution. The addition rate of 2N hydrochloric acid at this time was changed. Then, the dissolution was filtrated and washed with water. A powder was obtained by calcining the dissolution for 3 hours at 700° C.

TABLE 3

| Addition rate of hydrochloric acid | 2 ml/min | 120 ml/min |
|---|---|---|
| Time required for pH adjustment | 150 min | 2.5 min |
| Property | Fine-shaped mesoporous FIG. 5 | Rod-shaped mesoporous FIG. 2 |

As is clear from the result, the powder became fine mesoporous in the case where the addition rate of 2N-hydrochloric acid was 2 ml/min. Also, the powder became rod-shaped mesoporous in the case where the addition rate of 2N-hydrochloric acid was 120 ml/min.

As a result of the more detailed experiment, it is preferable that the addition rate of hydrochloric acid was 10 ml/min or more (30 min or less for the necessary time of pH adjustment), in said condition.

Acid Concentration of pH Adjustment

It is preferable to adjust the concentration of the acid for pH adjustment which was added in said condensation step so as that the powder can be formed in rod-shape in the present invention.

Namely, 0.5 mol of sodium metasilicate and 0.1 mol of behenyl trimethylammonium chloride (BTC) were dissolved to 1 liter of ion-exchanged water, as like the above. The temperature at this time was maintained at 70° C. The pH value of the mixture was adjusted to 8–9 with the various concentrations of the hydrochloric acid solution with 120 ml/min just after the dissolution. Then, the dissolution was filtrated and washed with water. A powder was obtained by calcining the dissolution for 3 hours at 700° C.

TABLE 4

Figure 7:

| Addition rate of hydrochloric acid | 0.2N | 2N | 5N |
|---|---|---|---|
| Time required for pH adjustment | 35 min | 2.5 min | 1 min |
| Property | Fine-shaped mesoporous FIG. 6 | Rod-shaped mesoporous FIG. 2 | Rod-shaped mesoporous FIG. 7 |

As is clear from the result, the powder was mesoporous in the case where 0.2N-hydrochloric acid was used, but the powder became nevertheless fine. It is preferable that the concentration of hydrochloric acid is 2N or more for obtaining a rod-shaped mesoporous powder. However, though a rod-shaped mesoporous powder was obtained in the case where 5N-hydrochloric acid was used, the powder was slightly crumbled. Accordingly, the concentration of hydrochloric acid is preferably 1–5N, and more preferably is about 1.5–3N.

In consideration with the result regarding the above-stated acid addition rate, it can be thought that the necessary time of the pH changing rate is prescribed the difference for forming rod-shaped or fine powder. In the case where the necessary time for pH adjustment at the time of sifting from the dissolution step to the condensation step was 30 minutes or more, the powder became fine. Also, in the case where the necessary time for pH adjustment was less than 30 minutes, the powder tended to become rod-shaped.

The values of property in the case where the various powders were prepared with the same process are shown in the following.

TABLE 5

| | Fine-shaped mesoporous powder | Rod-shaped mesoporous powder | Rod-shaped nonporous powder |
|---|---|---|---|
| $Na_2SiO_3$ | 0.5 mol/L | 0.5 mol/L | 1.5 mol/L |
| Acid addition rate | 2 mL/min | 120 mL/min | 120 mL/min |
| Specific surface area | 1100 m$^2$/g | 900 m$^2$/g | 50 m$^2$/g |
| Oil adsorption | 300 mL/100 g | 500 mL/100 g | 400 mL/100 g |
| Size of pore | 30Å | 35Å | — |

As is clear from TABLE 5, it is understood that though a rod-shaped mesoporous powder has a small specific surface area as compared with a fine mesoporous powder. The rod-shaped mesoporous powder has large oil adsorption and excellent oil adsorption property.

Also, said oil adsorption was measured as shown in the following according to Japanese Industrial Standard (JIS).

Namely, 1–5 g of a sample was taken to a center of a measurement board. Squalane was gradually instilled onto the sample with 4–5 drops at a time from a burette and the whole part was sufficiently rubbed with a spatula in each time. When the whole part of the sample became a hard mass in patty-like with repeatedly dropping and rubbing, squalane was rubbed with every single drop. And this operation was terminated at the time that the sample could be a spiral shape by using a spatula.

A mesoporous powder in accordance with the present invention has a protection effect and a controlled release effect for an inner material because the mesoporous powder has a superb oil adsorption property and large pores. Also, the mesoporous powder is expected to be useful a pharmaceutical carrier and a column packing or for cosmetics and foods.

Also, a rod-shaped powder aggregate in accordance with the present invention does not have pores, but it nevertheless has a large specific surface area. Consequently, peak-tailing due to the pore rarely occurs by using the rod-shaped powder aggregate as a column packing by introducing the various modified groups. Also, the rod-shaped powder aggregate can display a superb separability. Also, when the rod-shaped powder aggregate was observed with one particle, the rod-shaped powder aggregate had a structure which had a space in one particle because the rod-shaped powder was a network-state that i lot of rod were intertwined. Accordingly, the rod-shaped powder aggregate has, for example, excellent oil and water adsorption properties and is expected to be useful for pharmaceutical carriers or cosmetics, foods, and the like.

Also, with the mesoporous powder tailing hardly occurs since the mesoporous powder does not have the pores. Further, though a specific surface area of the rod-shaped powder is smaller than that of the fine mesoporous powder, but the rod-shaped powder nevertheless has a large amount of oil adsorption and a superb oil adsorption properties. Also, in considering that chemical modification occurs easily at an interface, though the specific surface area is relatively small, the rod-shaped powder nevertheless has a large amount of oil adsorption. This indicates that the rod-shaped powder can hold a large amount of an oily component in stable.

Further it is preferable to conduct a hydrophobic or hydrophilic surface treatment according to, for example, an inner material or using environment.

A more definite example of the present invention will be explained in the following.

EXAMPLE 1-1

0.5 mol of sodium metasilicate ($Na_2SiO_3$) and 0.1 mol of behenyl trimethylammonium chloride (BTC) were dissolved to 1 liter of ion-exchanged water. The temperature at this time was maintained at 70° C. The pH value of the mixture was adjusted to 8–9 by adding 2N hydrochloric acid with flow velocity of 120 ml/min just after the dissolution. Then, the dissolution was filtrated and washed with water. A powder was obtained by calcining the dissolution for 3 hours at 700° C.

Figure 8:
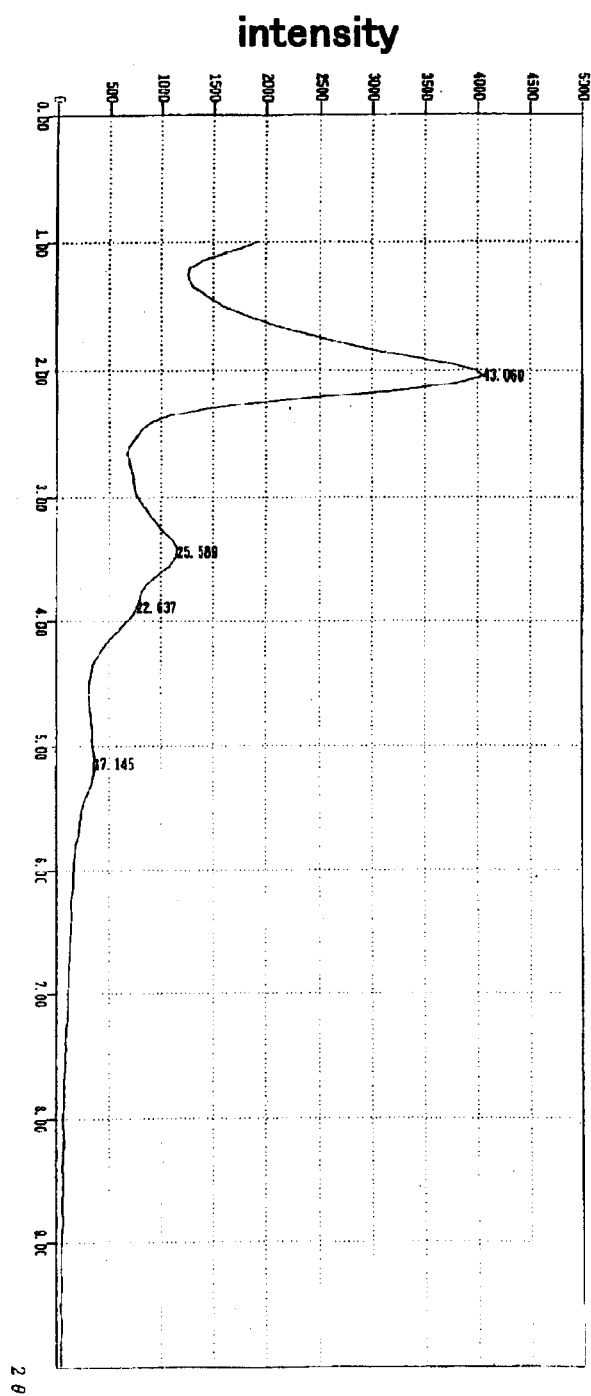
FIG. 8 is an X-ray diffraction diagram of a rod-shaped mesoporous powder which is obtained by the present invention.
Figure 9:
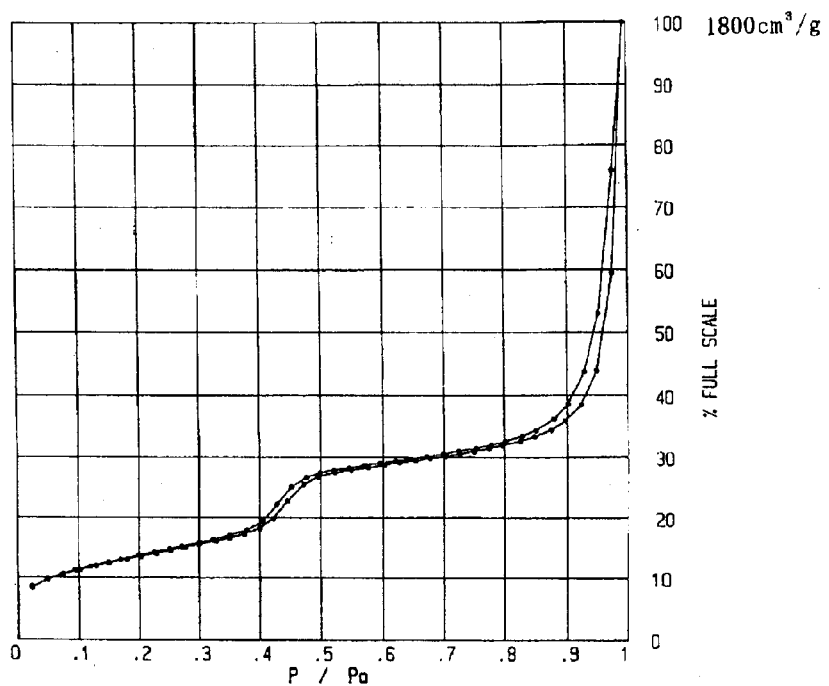
FIG. 9 is a nitrogen adsorption isotherm diagram of the rod-shaped mesoporous powder shown in FIG. 8.
Figure 10:
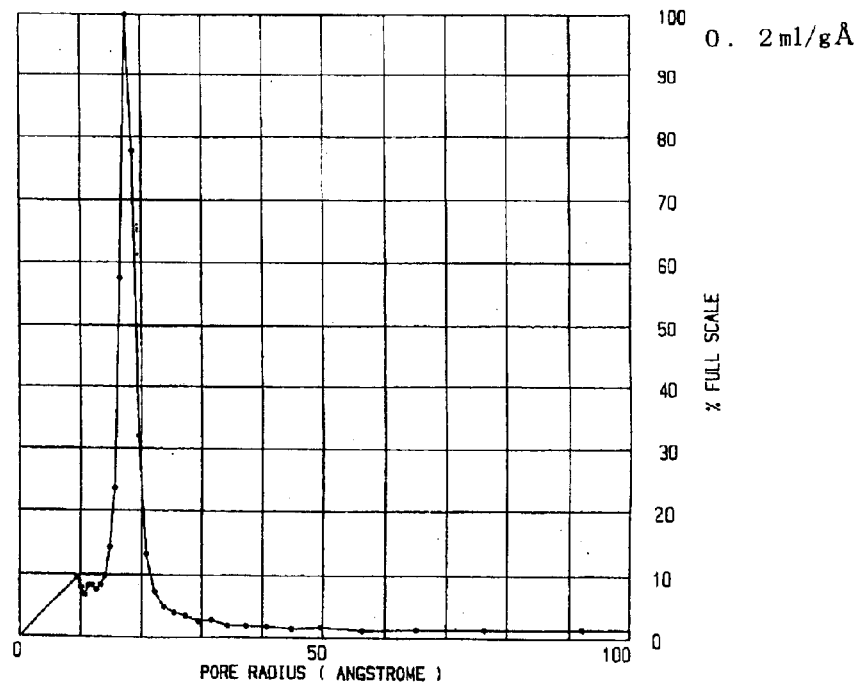
FIG. 10 is an explanatory view of a pore size distribution of the rod-shaped mesoporous powder shown in FIG. 8.

An X-ray diffraction diagram, a nitrogen adsorption isotherm and a pore size distribution which are obtained in this place are shown in FIG. 8, FIG. 9 and FIG. 10, respectively.

As shown in FIG. 8, diffraction strength shows four diffraction peaks which represents a hexagonal structure. Also, a steep rise in the vicinity of the relative vapor pressure (P/po)=0.45 of nitrogen adsorption isotherm which is shown in FIG. 9 represents the evenness of the pore size. More concretely, the evenness is clearly shown as the distribution of the pore size which was shown in FIG. 10.

EXAMPLE 1-2

0.5–1.2 mol of sodium metasilicate ($Na_2SiO_3$) and 0.05–0.24 mol of behenyl trimethyl ammonium chloride (BTC) were dissolved to 1 liter of ion-exchanged water. The temperature at this time was maintained at 70° C. The pH value of the mixture was adjusted to 8–9 by adding 2N-hydrochloric acid just after the dissolution. Then, the dissolution was filtrated and washed with water. A rod-shaped mesoporous powder was obtained by calcining the dissolution for 3 hours at 700° C.

Here, $Na_2SiO_3$/BTC was determined at 1/0.1–1/0.2. The rod-shaped mesoporous powder could be prepared when $Na_2SiO_3$/BTC was within this range.

EXAMPLE 1-3

0.5–1.2 mol of sodium metasilicate ($Na_2SiO_3$), 0.05–0.24 mol of stearyl trimethyl-ammonium chloride (STC) and 0.5–2 mol of sodium chloride (NaCl) were dissolved to 1 liter of ion-exchanged water. After this, a rod-shaped mesoporous powder was obtained by the same process with Example 2-2.

Here, $Na_2SiO_3$/STC/NaCl was determined at 1/0.1/1–4 to 1/0.2/1–2. The rod-shaped mesoporous powder could be prepared when $Na_2SiO_3$/STC/NaCl was within this range.

EXAMPLE 1-4

0.5–1.2 mol of sodium metasilicate ($Na_2SiO_3$), 0.05–0.24 mol of stearyl trimethyl-ammonium chloride (STC) and 0.5–2 mol of sodium bromide (NaBr) were dissolved to 1 liter of ion-exchanged water. After this, a rod-shaped mesoporous powder was obtained by the same process with Example 2-2.

Here, $Na_2SiO_3$/STC/NaBr was determined at 1/0.1/1–4 to 1/0.2/1–2. The rod-shaped mesoporous powder could be prepared when $Na_2SiO_3$/STC/NaBr was within this range.

EXAMPLE 1-5

0.5–1.2 mol of sodium orthosilicate ($Na_4SiO_4$) and 0.05–0.24 mol of behenyl-trimethylammonium chloride (BTC) were dissolved to 1 liter of ion-exchanged water. After this, a rod-shaped mesoporous powder was obtained by the same process with Example 2-2.

Here, $Na_4SiO_4$/BTC was determined at 1/0.1–1/0.2. The rod-shaped mesoporous powder could be prepared when $Na_4SiO_4$/BTC was within this range.

EXAMPLE 1-6

0.5–1.2 mol of sodium metasilicate ($Na_2SiO_3$), 0.05–0.24 mol of behenyl trimethyl-ammonium chloride (BTC) and 0–0.5 mol of silicon dioxide ($SiO_2$) were dissolved to 1 liter of ion-exchanged water. After this, a rod-shaped mesoporous powder was obtained by the same process with Example 2-2.

Here, $Na_2SiO_3+SiO_2$ was less than 1.3 mol. The rod-shaped mesoporous powder could be prepared when $Na_2SiO_3+SiO_2$ was within this range.

EXAMPLE 1-7

0.5–1.2 mol of sodium metasilicate ($Na_2SiO_3$), 0.05–0.24 mol of stearyl trimethyl-ammonium bromide (STB) and 0.2–2 mol of sodium bromide (NaBr) were dissolved to 1 liter of ion-exchanged water. After this, a rod-shaped mesoporous powder was obtained by the same process with Example 2-2.

Here, $Na_2SiO_3$/STB/NaBr was determined at 1/0.1/1–4 to 1/0.2/1–2. The rod-shaped mesoporous powder could be prepared when $Na_2SiO_3$/STC/NaBr was within this range.

II. Humectant Adsorbing Powder

The humectant adsorbing powder in accordance with the present invention is characterized in that a humectant is adsorbed to a mesoporous powder.

As a bar mesoporous powder, an optional powder which is usually combined to a cosmetic preparation can be used. For example, a bar whose outer diameter is 20~200 nm and a mesopore which is elongated in its longer direction is especially desirable for the stabilization effect of a product, the water holding effect, the moisturing effect of skin and the absorption effect of sweat and sebum.

Humectant

A humectant that is used in this invention is not limited, if it is compounded in a cosmetic preparation. For example, 1,3-buthyleneglycol, di-propylene glycol, glycerin, erythritol, xylitol 1,2-penta-diol, di-glycerin, polyoxyethylene methylglucoxide, sorbitol, polyethylene glycol (average molecular weight 400~20000) and so forth can be used as a humectant.

Manufacturing Process of Humectant Adsorbing Powder

Although the various methods are used as a manufacturing process of humectant adsorbing powder of this invention, for example the following manufacturing process is illustrated.

EXAMPLE 2-1

Glycerin Adosorbing Powder

Behenyl trimethyl ammonium chloride 0.01 mol was dissolved in 0.5M sodium methasilicate aqueous solution 100 mL. After the pH value of mixture was adjusted about 8 with hydrochloric acid, the dispersing solution was filtered and washed with water. The bar mesoporous powder was obtained by drying and baking (700° C.) the reminder.

The powder was added to EtOH solution of concentrated glycerin (humectant). After being dispersed completely, EtOH is removed with drying under reduced pressure, and predetermined concentration of the glycerin adsorbing bar mesoporous powder was obtained.

Although an example of a liquid humectant such as glycerin which was disolved in a solvent such as EtOH was explained in said Example 2-1, even in the case that humectant is a solid, it is desirable to select an appropriate solvent according to the kind of said humectant, and disolved in said solvent.

On the other hand, in the case that humectant is liquid, the following Example 2-2, that mesoporous powder is pulverized, added to a humectant, and adsorbs said humectant, is illustrated. The drying process and so forth is omitted in this method and the process is simplified.

EXAMPLE 2-2

Glycerin Adosorbing Powder

Behenyl trimethyl ammonium chloride 0.01 mol was dissolved to 0.5M sodium methesilicate aqueous solution 100 mL. After the pH value of mixture was adjusted about 8 with hydrochloric acid, the dispersing solution was filtered and washed with water. The bar mesoporous powder was obtained by drying and baking the reminder at 700° C.

The powder was pulverized by pulverizer, and added to concentrated glycerin. After dispersing completely, a predetermined concentration of the glycerin adsorbing bar mesoporous powder was obtained.

Adsorbing Rate

Next, glycerin adsorbing rate (wt %) to the total of glycerin adsorbing powder was changed and the quantitative relation was evaluated about glycerin adsorbing powder manufactured by said Example 2-1.

<Evaluation Method>

⊚: very good

○: good

Δ: slightly good

X: bad

TABLE 6

| adsorbing rate | 0.5 | 1.0 | 10 | 30 | 50 | 70 | 90 | 95 |
|---|---|---|---|---|---|---|---|---|
| moisturing effect | X | ○ | ⊚ | ⊚ | ⊚ | ⊚ | ⊚ | ⊚ |
| absorption effect of sweat and sebum | ⊚ | ⊚ | ⊚ | ⊚ | ⊚ | ⊚ | ○ | X |

As is clear from Table 6, when the glycerin adsorbing rate to the total of glycerin adsorbing powder falls below 1 wt %, the actual moisturing effect disappears. When the glycerin adsorbing rate to the total of glycerin adsorbing powder exceeds 90 wt %, the absorption of sweat and sebum by the powder can not be obtained.

Therefore, to maintain an appropriate balance of the moisturing effect and the absorption effect of sweat and sebum, a humectant adsorbing rate to the total of glycerin adsorbing powder is 1~90 wt %, especially 10~70 wt % is desirable.

Water Holding Effect

Figure 11:
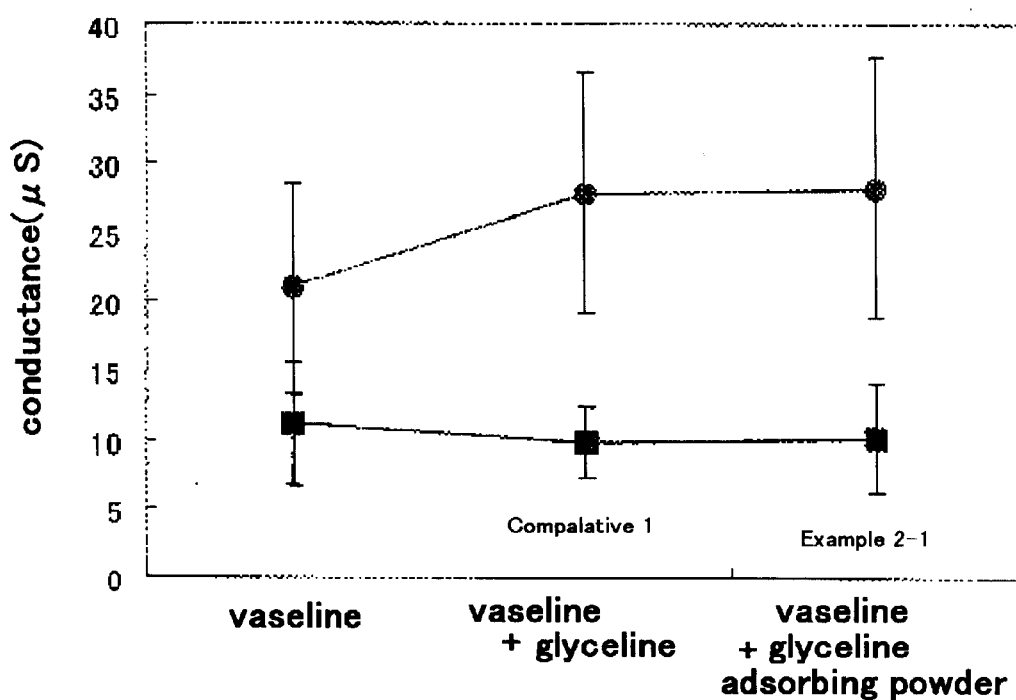
FIG. 11 is an explanatory view of water holding effect of a glycerin adsorbing mesoporous powder that is the humectant adsorbing powder in accordance with the present invention.

The comparative result is shown in a FIG. 11 between in the case that glycerin adsorbing powder manufactured in Example 2-1 was used, and in the case that glycerin was used (Comparative 1).

In this comparative test, in order to examine a water holding effect of glycerin adsorbing powder itself, glycerin 10% (Comparative 1), and 50% glycerin adsorbing powder 20% (Example 2-1) was mixed with vaseline by 3 rollers, and used as samples.

Each 2 mg/cm² sample was applied by a finger to the size of 4×5 cm in side arm, and the conductance before and after application were measured.

SKICON-200 (manufactured by I.B.S company) was used for measurement, and evaluated with the average of 10 optional points of application.

It is clear in FIG. 11, that the case of using vaseline and glycerin (Comparative 1) and the case of using vaseline and glycerin adsorbing powder (Example 2-1), conductance after application is remarkably higher than that before in comparison with the case of using only vaseline.

From this case, it was confirmed that a humectant adsorbing powder in this invention itself demonstrates an excellent water holding effect at the time of use.

More definite examples of the present invention will be explained in the following examples.

The following humectant adsorbing powders were useful for the stabilization effect of product, the moisturing impression, the fitting impression, and the prevention effect of being dirty by sweat.

EXAMPLE 2-3

Xylitol Adosorbing Powder

Stearyl trimethyl ammonium bromide 0.01 mol was dissolved to 0.5M sodium methasilicate aqueous solution 100 mL. After the pH value of mixture was adjusted about 8 with hydrochloric acid, the dispersing solution was filtered and washed with water. The bar mesoporous powder was obtained by drying and baking the reminder at 700° C.

The powder was added to EtOH solution of xylitol. After it was dispersed completely, EtOH was removed with drying under reduced pressure and a predetermined concentration of the xylitol adsorbing bar mesoporous powder was obtained.

EXAMPLE 2-4

1,3-buthyleneglycol Adosorbing Powder

Stearyl trimethyl ammonium chloride 0.01 mol and bromine chloride 0.01 mol were dissolved to 0.5M sodium methasilicate aqueous solution 100 mL. After the pH value of mixture was adjusted to about 8 with hydrochloric acid, the dispersing solution was filtered and washed with water. The bar mesoporous powder was obtained by drying and baking the reminder at 700° C.

The powder was added to EtOH solution of 1,3-buthyleneglycol. After dispersing completely, EtOH was removed with drying under reduced pressure, and a predetermined concentration of the 1,3-buthyleneglycol adsorbing bar mesoporous powder was obtained.

III. Powder Cosmetic Preparation

The powder cosmetic preparation comprising said humectant adsorbing powder such as a solid white powder, a solid white powder, a powdery foundation, a dual purpose foundation, a cake type foundation, an oily foundation, an eye shadow and so forth are shown as examples of the powder cosmetic preparation in this invention.

Manufacturing Process of Cosmetic Preparation

As an example of the powder cosmetic preparation in this invention, a manufacturing process of the dual purpose foundation comprising 50% glycerin adsorbing powder manufactured in said Example 2-1 is shown below.

EXAMPLE 3-1

Dual Purpose Foundation

| | |
|---|---|
| 50% glycerin adsorbing powder | 20.0 wt % |
| siliconizing talc | 9.2 |
| siliconizing mica | 30.0 |
| siliconizing titanium oxide | 15.0 |
| siliconizing microcrystalline titanium oxide | 5.0 |
| siliconizing red iron oxide | 1.0 |

-continued

| | |
|---|---|
| siliconizing yellow iron oxide | 3.0 |
| siliconizing black iron oxide | 0.2 |
| zinc stearate | 0.1 |
| nylon powder | 2.0 |
| squalane | 4.0 |
| solid paraffin | 0.5 |
| dimethyl polysiloxane | 4.0 |
| glycerin tri-iso octanoate | 5.0 |
| octyl methoxy cinnamate | 1.0 |
| antiseptic agent, antioxidant | q.s |
| perfume | q.s |

The Manufacturing Process

Talc and color pigment are mixed by a blender. The remaining powder material is added to the mixture, and mixed well and add a binder and an antiseptic agent. After adjusting the color and spraying perfume, it is homogeneously mixed. After pulverizing with pulverizer, it is filtered and compressed in a plate of the case.

A dual purpose foundation comprising a glycerin adsorbing powder of this invention obtained by above process was useful for stabilization, moisturing impression that substitutes for oil at the time of use, and prevention of being dirty by sweat.

Mixing Quantity

Next, the mixing quantity of glycerin adsorbing powder to the total of a dual purpose foundation was changed and quantitative relation was evaluated about dual purpose foundation manufactured by said Example 3-1.

<Evaluation Method>

⊙: very good

○: good

Δ: slightly good

X: bad

TABLE 7

| mixing quantity | 0.05 | 0.1 | 1.0 | 10 | 30 | 50 | 70 | 90 | 95 |
|---|---|---|---|---|---|---|---|---|---|
| moisturing effect | X | ○ | ○ | ⊙ | ⊙ | ⊙ | ⊙ | ⊙ | ⊙ |
| productability of the product | ⊙ | ⊙ | ⊙ | ⊙ | ⊙ | ⊙ | ⊙ | ○ | X |

As is clear from Table 7, when the mixing quantity of glycerin adsorbing powder to the total of a two way foundation falls below 0.1 wt %, the actual moisturing effect disappears. When the mixing quantity of glycerin adsorbing powder to the total of a two way foundation exceeds 90 wt %, a product does not exist.

Therefore, mixing quantity of a humectant adsorbing powder to the total of a powder cosmetic preparation is 1~90 wt %, especially 10~70 wt % is desirable.

Stability of Powder Cosmetic Preparation

For the purpose of examining the stability of the powder cosmetic preparation in this invention, dual purpose foundation shown in the following Table 8 was prepared and a comparative test was conducted. Stability with the passage of time of each product was compared at 40° C. and relative humidity of 93%.

In the case that glycerin was combined (Comparative 2), the dual purpose foundation expanded and the drop of water appeared on the surface of said foundation one day later.

In the case that each components such as glycerin and mesoporous powder are combined simultaneously substantially with other components (Comparative 3), the dual purpose foundation expanded and the drop of water appeared on the surface of said foundation about 36 hours later.

In the case that glycerin adsorbing silica gel is combined (Comparative 4), the dual purpose foundation expanded and the drop of water appeared on the surface of said foundation, although it is later than Comparative 2,3.

In comparison with these cases, in the case that glycerin adsorbing powder manufactured in said Example 2-1 is combined (Example 3-1), although increase of the mass was observed with the passage of time, it almost became flat in 2 weeks. The dual purpose foundation did not expand and the drop of water did not appear on the surface of said foundation.

From the result, by previously adsorbing glycerin into bar mesoporous powder, the dual purpose foundation combined a glycerin adsorbing powder in this invention was useful for the stabilization.

Water Holding Effect at the Time of Use

Next, to examine the water holding effect of a powder cosmetic preparation in this invention, a comparative test by using dual purpose foundation shown in the following Table 8 was conducted.

Each 2 mg/cm$^2$ sample i.e. dual purpose foundation manufactured in Comparative 5 and Example 3-1 was applied by finger to the size of 4×5 cm on an arm side, and the conductance before and after application were measured.

SKICON-200 (manufactured by I.B.S company) was used for measurement, and evaluated with an average of 10 optional points of application.

Figure 12:
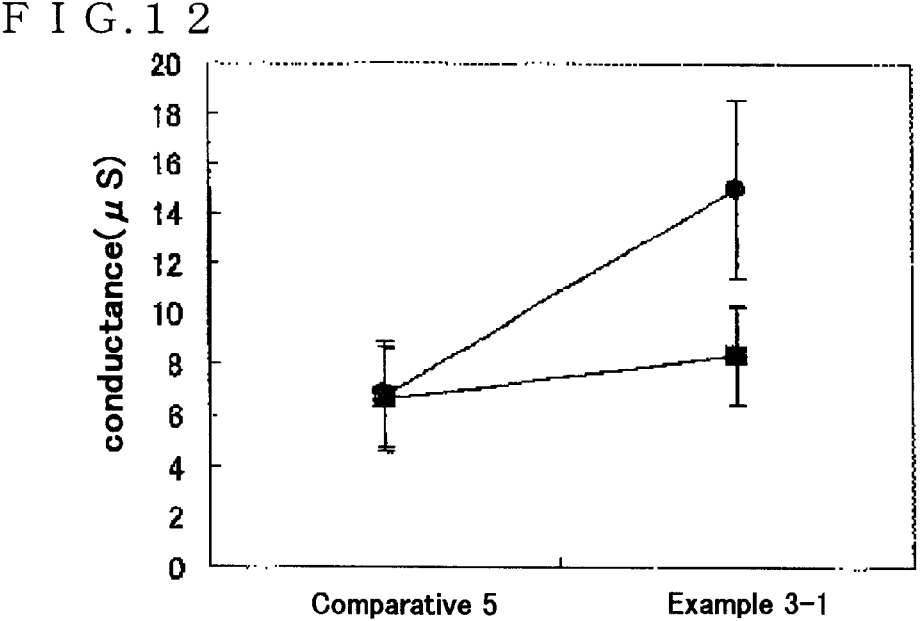
FIG. 12 is an explanatory view of water holding effect of the dual purpose foundation comprising a glycerin adsorbing mesoporous powder that is the cosmetic preparation in accordance with the present invention.

It is clear in FIG. 12, that in the case of not comprising glycerin (Comparative 5), conductance after application is not higher than conductance before application, and a water holding effect is not present.

In the case of a dual purpose foundation comprising glycerin adsorbing powder in this invention, conductance after application is improved largely comparing with conductance before application.

From this case, by previously adsorbing glycerin into bar mesoporous powder, it is shown that a water holding effect of foundation is excellent.

Stability

Next, to examine stability of the powder cosmetic preparation in this invention, a comparative test by using dual purpose foundation shown in the following Table 8 was conducted.

The case that glycerin adsorbing powder manufactured in said Example 2-1 is combined (Example 3-1) is excellent in terms of stability, compared with the case that glycerin is combined as it is (Comparative 2), the case that each components such as glycerin and mesoporous powder are combined simultaneously with other components (Comparative 3), the case that glycerin adsorbing silica gel is combined (Comparative 4), and the case that glycerin and mesoporous powder is not combined (Comparative 5).

From this case, by previously adsorbing glycerin into bar mesoporous powder, it is shown that it is excellent in stability.

<Evaluation Method>

⊙: very good

○: good

Δ: slightly good

X: bad

TABLE 8

|  | Example 3-1 | Comparative 2 | Comparative 3 | Comparative 4 | Comparative 5 |
|---|---|---|---|---|---|
| 50% glycerin adsorbing powder | 20.0 | | | | |
| glycerin | | 20.0 | 10.0 | | |
| mesoporous powder | | | 10.0 | | |
| 50% glycerin adsorbing silica gel | | | | 20.0 | |
| siliconizing talc | 9.2 | 9.2 | 9.2 | 9.2 | 9.2 |
| siliconizing mica | 30.0 | 30.0 | 30.0 | 30.0 | 40.0 |
| siliconizing titanium oxide | 15.0 | 15.0 | 15.0 | 15.0 | 15.0 |
| siliconizing microcrystalline titanium oxide | 5.0 | 5.0 | 5.0 | 5.0 | 5.0 |
| siliconizing red iron oxide | 1.0 | 1.0 | 1.0 | 1.0 | 1.0 |
| siliconizing yellow iron oxide | 3.0 | 3.0 | 3.0 | 3.0 | 3.0 |
| siliconizing black iron oxide | 0.2 | 0.2 | 0.2 | 0.2 | 0.2 |
| zinc stearate | 0.1 | 0.1 | 0.1 | 0.1 | 0.1 |
| nylon powder | 2.0 | 2.0 | 2.0 | 2.0 | 2.0 |
| squalane | 4.0 | 4.0 | 4.0 | 4.0 | 4.0 |
| solid paraffin | 0.5 | 0.5 | 0.5 | 0.5 | 0.5 |
| dimethyl polysiloxane | 4.0 | 4.0 | 4.0 | 4.0 | 4.0 |
| glycerin tri-iso octanoate | 5.0 | 5.0 | 5.0 | 5.0 | 5.0 |
| octyl methoxy cinnamate | 1.0 | 1.0 | 1.0 | 1.0 | 1.0 |
| antiseptic agent, antioxidant | q.s | q.s | q.s | q.s | q.s |
| perfume | q.s | q.s | q.s | q.s | q.s |
| stability of a product | ◎ | X | X | X | ◎ |
| moisturing effect | ◎ | ◎ | ○ | Δ | X |
| durability | ◎ | X | ○ | Δ | X |

The Manufacturing Process

Talc and color pigment are mixed by a blender. The remaining powder material is added to the mixture, and mixing well and adding a binder and an antiseptic agent. After adjusting the color of the mixture perfume adds in said mixture and mixing homogeneously. The mixture was pulverized with pulverizer, filtered and compressed in a plate of the case.

Moisture Effect and Skin Roughness Improvement Effect

To examine moisturing effect and roughness improvement effect of skin, a comparative test by using powdery foundation like following Table 4 was conducted.

A cup containing 20 ml of enter is pushed to a side of an arm and left 10 minutes to make the skin rough.

After applying each 50 mg of powdery foundation of Comparative 6 and this invention to a side of an arm with in a 4 cm diameter circle by a powder puff, variation with passage of time of conductance was measured.

SKICON-200 (manufactured by I.B.S company) was used to measure, and evaluate with the average of 10 optional points of application.

Figure 13:
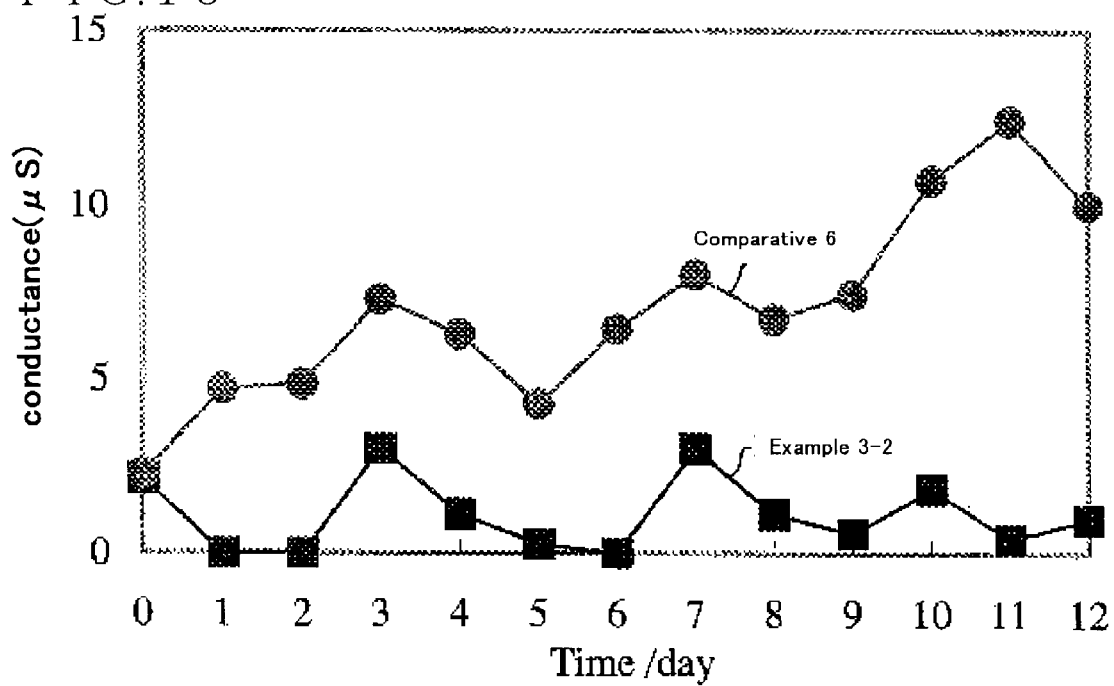
FIG. 13 is an explanatory view of water holding effect and skin roughness improvement effect of the powdery foundation comprising a glycerin adsorbing mesoporous powder that is the cosmetic preparation in accordance with the present invention.
Figure 14:
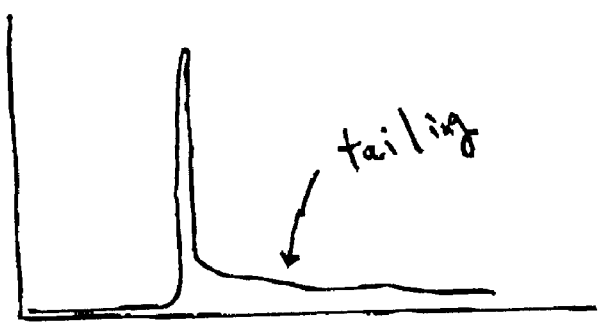
FIG. 14 is a pictorial representation of tailing, the slow transfer phenomenon of the remainder part that is seen after the transfer of the principal part of the component in chromatography.

It is clear in FIG. 13 that in the case of using squalane instead of glycerin adsorbing powder (Comparative 6), a moisturing effect and a skin roughness improvement effect is not improved substantially.

In the case of using glycerin adsorbing powder in this invention (Example 3-2), the moisturing effect and the skin roughness improvement effect are improved largely with time, because conductance has improved.

From this case, by previously adsorbing glycerin to bar mesoporous powder, it is conceivable that it has excellent moisturing effect and skin roughness improvement effect, also the foundation is excellent in a water holding effect.

Furthermore, the foundation in this invention is useful for moisturing effect instead of oil such as squalane at the time of use.

TABLE 9

|  | Example 3-2 | Comparative 6 |
|---|---|---|
| talc | 40.3 | 24.3 |
| mica | 15.0 | 15.0 |
| kaolin | 5.0 | 5.0 |
| titanium oxide | 10.0 | 10.0 |
| titanium mica | 3.0 | 3.0 |
| 50% glycerin adsorbing powder | 10.0 | 10.0 |
| zinc stearate | 1.0 | 1.0 |
| red iron oxide | 1.0 | 1.0 |
| yellow iron oxide | 3.0 | 3.0 |
| black iron oxide | 0.2 | 0.2 |
| nylon powder | 10.0 | 10.0 |
| squalane | 6.0 | 30.0 |
| lanolin acetate | 1.0 | 1.0 |
| octyl dodecyl myristate | 2.0 | 2.0 |
| neo-pentylglycol di-iso octanoate | 2.0 | 2.0 |
| sorbitan mono-oleate | 0.5 | 0.5 |
| antiseptic agent, antioxidant | q.s | q.s |
| perfume | q.s | q.s |

The Manufacturing Process

Talc and color pigment are mixed by a blender. The remaining powder material is added to the mixture, and mixed well and add a binder and an antiseptic agent. After adjusting the color and spraying perfume, it is homogeneously mixed. After pulverizing with pulverizer, it is filtered and compressed in a plate of the case.

Prevention Effect of Being Dirty by Sweat

To examine the stability effect of the powder cosmetic preparation in this invention, the following comparative test was conducted.

Each dual purpose foundation in Comparative 5 and Example 3-1 was applied to half of the face of each 6 panelist of A~F. After playing tennis for one hour under the blazing heat in midsummer, the effect of being dirty was compared.

The evaluation of this invention compared with Comparative 5 is shown to Table 10.

<Evaluation Method>
1: good
2: slightly good
3: same
4: slightly bad
5: bad

TABLE 10

| panelist | A | B | C | D | E | F |
|---|---|---|---|---|---|---|
| dusty skin feel | 2 | 2 | 2 | 2 | 1 | 1 |
| twist | 2 | 1 | 1 | 2 | 1 | 1 |
| sebaceous skin feel | 2 | 3 | 2 | 2 | 3 | 2 |
| fading | 2 | 3 | 2 | 2 | 3 | 2 |
| turbidity | 1 | 2 | 3 | 1 | 2 | 2 |

As is clear in table 10, many improvements are seen in the case that used foundation in this invention in comparison with the case that used foundation Comparative 5.

From this case, by previously adsorbing glycerin into bar mesoporous powder, and preparing glycerin adsorbing powder, it is shown that prevention effect of being dirty by sweat is excellent.

Prevention Effect of Drop of Sweat

As the stability effect of powder cosmetic preparation in this invention, the following comparative test was conducted.

Each dual purpose foundation in Comparative 5 and Example 3-1 was applied to half of the face of each 6 panelist of A~F. After playing tennis for one hour under the blazing heat in midsummer the effect of drop of sweat was compared.

The evaluation of this invention compared with Comparative 5 is shown to Table 11.

<Evaluation Method>
1: good
2: slightly good
3: same
4: slightly bad
5: bad

TABLE 11

| panelist | A | B | C | D | E | F |
|---|---|---|---|---|---|---|
| beads of sweat | 1 | 2 | 1 | 2 | 1 | 1 |
| drip of sweat | 1 | 1 | 1 | 1 | 1 | 1 |

As is clear in table 11, many improvements are seen in the case that used foundation in this invention in comparison with the case that used foundation Comparative 5.

From this case, by previously adsorbing glycerin into bar mesoporous powder, and preparing glycerin adsorbing powder, it is shown that prevention of the effect of drop of sweat is excellent.

The powder cosmetic preparation of this invention has composite improvement mechanism, and it is not clarified yet for details.

However, it is not the effect that is obtained easily, even if it is in ①–③.

① In the case that humectant is combined with powder cosmetic preparation as it is (Comparative2).

② In the case that humectant and mesoporous powder are combined with powder cosmetic preparation simultaneously substantially with other components (Comparative3), ③ In the case that other humectant adsorbing mesoporous powder such as humectant adsorbing silica gel is combined with powder cosmetic preparation (Comparative4).

By previously adsorbing humectant into bar mesoporous powder, and preparing a humectant adsorbing powder, bar mesoporous powder and humectant can work sufficiently. Because humectant is able to be dispersed homogeneously with the requested concentration without received the influence of other component.

Specifically, the reason is shown in the following.

During Preservation

In a powder cosmetic preparation using the humectant adsorbing powder in this invention, the humectant is retained firmly within mesopours, because said humectant adsorbing powder was made from a bar mesoporous powder that has mesopours whose open aperture size and capacity are homogeneous.

Moreover, the bar mesoporous powder exists greatly in a lump form which each humectant adsorbing powder stuck perfectly together in a powder cosmetic preparation during preservation. The outside diameter of a bar mesoporous powder is very homogeneous.

Therefore, the pore of each powder is occupied substantially during preservation. The humectant inside the pores makes it difficult to absorb the moisture in the atmosphere.

Moreover, even if the humectant absorbs the moisture in the atmosphere after a long time, said humectant make it difficult to extrude to moisture because it is retained firmly within the pores. The sweating of the product is prevented.

Moreover, because the humectant is retained firmly within the pore, even if humectant inside the pore expands, the expanding of the product is prevented, because the external form of powder itself does not change.

In the case that humectant and mesoporous powder are combined with a powder cosmetic preparation simultaneously with other components (Comparative3), the other components have been adsorbed to mesoporous powder previously. This causes the number of the mesoporous that can adsorb humectant to decrease.

Because of this, without being adsorbed to mesoporous powder, the humectant becomes the cause of sweating and expansion.

In the case that other humectant adsorbing mesoporous powder such as humectant adsorbing silica gel is combined with powder cosmetic preparation (Comparative4), there is dispersion in the size of the open aperture and capacity of the mesoporous. Because the humectant is not firmly adsorbed within the mesopores of powder, the mesoporous itself is not finely formed, and the stability of the product falls off.

At the Time of Use

The powder cosmetic preparation comprising the humectant adsorbing powder in this invention is excellent in water holding effect of humectant adsorbing powder and moisturing effect of skin. Moreover, the appropriate balance of moisturing effect and absorption effect of sweat and sebum can be maintained.

In other words, it is excellent in water holding effect of powder cosmetic preparation and moisturing effect, because the humectant, that is firmly adsorbed with the mesoporous of humectant adsorbing powder is ordinary discharged in a fixed quantity from the mesopores.

On the other hand, when excessive sweat and sebum was secreted, the mesoporous humectant adsorbing powder adsorbs it, so the retention power on the skin is improved.

In the case that other humectant adsorbing mesoporous powder such as humectant adsorbing silica gel is combined with a powder cosmetic preparation (Comparative4), there is dispersion in the size of the opening aperture and capacity of the mesoporous. Because the humectant is not adsorbed within the mesopores of powder firmly and sufficiently, the stability of the product falls off. Even this balance is lost between the moisturing effect and an absorption of sweat and sebum.

Comparing the case that humectant is combined as it is, and the case that each component such as mesoporous powder and humectant is combined at the same time as other components, the moisturing effect at the time of use and the stabilization can be obtained in the case of this invention.

Furthermore, a powder cosmetic preparation in this invention may combine with powder other than the above within quantitative and qualitative range where it does not damage the effect of this invention.

More definite examples of the present invention will be explained in the following.

The following powder cosmetic preparations were useful for the stabilization effect of the product, the moisturing effect, the fitting impression, and the prevention effect of being dirty by sweat.

EXAMPLE 3-3

White Powder

| | |
|---|---|
| talc | 50.0 wt % |
| kaolin | 5.0 |
| titanium oxide | 3.0 |
| zinc myristate | 5.0 |

| | |
|---|---|
| magnesium carbonate | 5.0 |
| sericite | 7.0 |
| 50% glycerin adsorbing powder | 20.0 |
| organo polysiloxane elastomer spherical powder | 2.0 |
| spherical silica | 3.0 |
| color pigment | q.s |
| perfume | q.s |

The Manufacturing Process

Talc and color pigment are mixed by a blender. The remaining powder material is added to the mixture, and mixed well. After adjusting the color and spraying perfume, it is homogeneously mixed. After pulverizing with pulverizer, it is filtered.

EXAMPLE 3-4
Solid White Powder

| | |
|---|---|
| talc | 10.0 wt % |
| kaolin | 5.0 |
| titanium oxide | 5.0 |
| zinc myristate | 5.0 |
| magnesium carbonate | 5.0 |
| sericite | 15.0 |
| 80% 1,3-buthyleneglycol adsorbing mesoporous powder | 50.0 |
| color pigment | q.s |
| squalane | 3.0 |
| glycerin tri-iso octanoate | 2.0 |
| antiseptic agent, antioxidant | q.s |
| perfume | q.s |

The Manufacturing Process

Talc and color pigment are mixed by a blender. The remaining powder material is added to the mixture, and mixed well and add a binder and an antiseptic agent. After adjusting the color and spraying perfume, it is homogeneously mixed. After pulverizing with pulverizer, it is filtered and compressed in a plate of the case.

EXAMPLE 3-5
Powdery Foundation

| | |
|---|---|
| talc | 10.3 wt % |
| mica | 15.0 |
| kaolin | 5.0 |
| titanium oxide | 10.0 |
| titanium mica | 3.0 |
| 50% glycerin adsorbing powder | 40.0 |
| zinc stearate | 1.0 |
| red iron oxide | 1.0 |
| yellow iron oxide | 3.0 |
| black iron oxide | 0.2 |
| nylon powder | 10.0 |
| squalane | 6.0 |
| lanolin acetate | 1.0 |
| octyl dodecyl myristate | 2.0 |
| neo-pentyl glycol di-iso octanoate | 2.0 |
| sorbitan mono-oleate | 0.5 |
| antiseptic agent, antioxidant | q.s |
| perfume | q.s |

The Manufacturing Process

Talc and color pigment are mixed by a blender. The remaining powder material is added to the mixture, and mixed well and add a binder and an antiseptic agent. After adjusting the color and spraying perfume, it is homogeneously mixed. After pulverizing with pulverizer, it is filtered and compressed in a plate of the case.

EXAMPLE 3-6
Cake-type Foundation

| | |
|---|---|
| talc | 28.1 wt % |
| kaolin | 10.0 |
| titanium oxide | 3.8 |
| sericite | 10.0 |
| zinc flower | 7.0 |
| 60% di-propylene glycol adsorbing mesoporous powder | 20.0 |
| red iron oxide | 1.0 |
| yellow iron oxide | 3.0 |
| black iron oxide | 0.2 |
| squalane | 8.0 |
| sorbitan POE mono-oleate | 3.0 |
| iso-cetyl octanoate | 2.0 |
| iso-stearic acid | 4.0 |
| antiseptic agent antioxidant | q.s |
| perfume | q.s |

The Manufacturing Process

Talc and color pigment are mixed by a blender. The remaining powder material is added to the mixture, and mixed well and add a binder and an antiseptic agent. After adjusting the color and spraying perfume, it is homogeneously mixed. After pulverizing with pulverizer, it is filtered and compressed in a plate of the case.

EXAMPLE 3-7
Oily Foundation

| | |
|---|---|
| talc | 12.8 wt % |
| kaolin | 5.0 |
| titanium oxide | 10.0 |
| 50% glycerin adsorbing powder | 20.0 |
| red iron oxide | 1.0 |
| yellow iron oxide | 3.0 |
| black iron oxide | 0.2 |
| solid paraffin | 3.0 |
| microcrystalline wax | 6.0 |
| bees wax | 2.0 |
| vaseline | 12.0 |
| lanolin acetate | 1.0 |
| squalane | 6.0 |
| iso-propyl palmitate | 18.0 |
| antioxidant | q.s |
| perfume | q.s |

The Manufacturing Process

A binder and antioxidant was dissolved at 85° C. The powder materials are mixed well and added to the mixture, grinding and dispersing by a colloid mill. After adding perfume and exhausting, it is poured to a container at 70° C. and cooled.

EXAMPLE 3-8
Eye Shadow

| | |
|---|---|
| talc | 35.0 wt % |
| mica | 15.0 |
| sericite | 5.0 |
| pigment | 15.0 |
| pearl pigment | 10.0 |
| 50% glycerin adsorbing powder | 20.0 |
| antiseptic agent | q.s |
| liquid paraffin | 6.0 |
| methyl polysiloxane | 2.0 |
| sorbitan sesqui-oleate | 2.0 |
| antioxidant | q.s |
| perfume | q.s |

The Manufacturing Process

The powder materials are mixed by a blender. After dissolving homogeneously the binder is added to the mixture, mixing well, pulverizing with pulverizer, and compressed it in a plate of the case.

What is claimed is:

1. A rod-shaped mesoporous powder which is mainly composed of silicon oxide and which has homogenous pore, and which is obtained by a process comprising the steps of;

a dissolution step wherein a concentration of 0.3–1.2M of a silicate which is in the range of $0<SiO_2/Y_2O<2$ (Y: alkali metal atom) is dissolved in the presence of a cationic surfactant and the pH is 11 or more, a condensation step wherein the pH is adjusted to 10.5 or less within 30 minutes, a rod micelle is formed with said cationic surfactant and a silicate is condensed on said rod micelle, and a removal step wherein said cationic surfactant is removed from a micelle state condensation which has an outer shell made of the silicate by said condensation.

2. A rod-shaped mesoporous powder according to claim 1, whose outer diameter is 20–200 nm and a mesopore is elongated to its longer direction.

3. A rod-shaped mesoporous powder according to claim 1, wherein a primary particle is formed by aggregating two or more of rod substances in network state.

4. A humectant adsorbing powder comprising a rod-shaped mesoporous powder and a humectant adsorbed in the powder which a humectant is adsorbed to a rod-shaped mesoporous powder according to claim 1.

5. A humectant adsorbing powder according to claim 4, wherein the adsorption rate of said humectant is 1 to 90% by weight % of the total of a humectant adsorbing powder.

6. A cosmetic preparation comprising a humectant adsorbing powder of claim 4.

7. A cosmetic preparation according to claim 6, wherein the content of humectant adsorbing powder is 0.1 to 90% by weight of the total of a cosmetic preparation.

8. A humectant adsorbing powder comprising a rod-shaped mesoporous powder and a humectant adsorbed in the powder which a humectant is adsorbed to a rod-shaped mesoporous powder according to claim 3.

9. A humectant adsorbing powder according to claim 8, wherein the adsorption rate of said humectant is 1 to 90% by weight % of the total of a humectant adsorbing powder.

10. A cosmetic preparation comprising a humectant adsorbing powder of claim 8.

11. A cosmetic preparation according to claim 10, wherein the content of humectant adsorbing powder is 0.1 to 90% by weight of the total of a cosmetic preparation.

* * * * *